US008715573B2

(12) United States Patent
Ball et al.

(10) Patent No.: US 8,715,573 B2
(45) Date of Patent: May 6, 2014

(54) FLUIDIC SYSTEM FOR A FLOW CYTOMETER WITH TEMPORAL PROCESSING

(75) Inventors: Jack T. Ball, Bellevue, WA (US); Collin A. Rich, Ypsilanti, MI (US)

(73) Assignee: Accuri Cytometers, Inc., Ann Arbor, MI (US)

( * ) Notice: Subject to any disclaimer, the term of this patent is extended or adjusted under 35 U.S.C. 154(b) by 734 days.

(21) Appl. No.: 11/872,676

(22) Filed: Oct. 15, 2007

(65) Prior Publication Data

US 2008/0152542 A1  Jun. 26, 2008

Related U.S. Application Data

(60) Provisional application No. 60/829,300, filed on Oct. 13, 2006.

(51) Int. Cl.
*G01N 21/00* (2006.01)
*G01N 21/01* (2006.01)

(52) U.S. Cl.
USPC ............... 422/81; 422/73; 422/82; 422/68.1

(58) Field of Classification Search
USPC ...................... 422/73, 68.1, 81, 82
See application file for complete search history.

(56) References Cited

U.S. PATENT DOCUMENTS

| 3,347,273 A | 10/1967 | Russell |
| 3,601,128 A | 8/1971 | Hakim |
| 3,672,402 A | 6/1972 | Bloemer |
| 3,819,272 A | 6/1974 | Crozier et al. |
| 4,112,735 A | 9/1978 | McKnight |
| 4,138,879 A | 2/1979 | Liebermann |
| 4,371,786 A | 2/1983 | Kramer |
| 4,448,538 A | 5/1984 | Mantel |
| 4,559,454 A | 12/1985 | Kramer |
| 4,570,639 A | 2/1986 | Miodownik |
| 4,691,829 A | 9/1987 | Auer |
| 4,755,021 A | 7/1988 | Dyott |
| 4,790,653 A | 12/1988 | North, Jr. |
| 4,818,103 A | 4/1989 | Thomas et al. |
| 4,824,641 A | 4/1989 | Williams |

(Continued)

FOREIGN PATENT DOCUMENTS

| EP | 466490 A | 1/1992 |
| EP | 1391611 A | 2/2004 |

(Continued)

*Primary Examiner* — Paul Hyun
*Assistant Examiner* — Robert Eom
(74) *Attorney, Agent, or Firm* — Jeffrey Schox

(57) ABSTRACT

The fluidic system 10 of the preferred embodiment includes a sheath pump 12 to pump sheath fluid 14 from a sheath container 16 through a sample port 34 into an interrogation zone 18 and a waste pump 20 to pump the sheath fluid 14 and a sample fluid 26 as waste fluid 22 from the interrogation zone 18 into a waste container 24, and a processor 30 to calculate a time window based on the flow rate of the sample fluid 26. Preferably the processor 30 also calculates a time window for the sample fluid to reach the interrogation zone 18 from the sample port 34 based on the flow rate of the sample fluid 26. The interrogation zone 18 functions to provide a location for the fluidic system 10 and an optical analysis system 32 of the flow cytometer to cooperatively facilitate the analysis of the sample fluid 26.

21 Claims, 2 Drawing Sheets

(56) References Cited

U.S. PATENT DOCUMENTS

| | | |
|---|---|---|
| 4,826,660 A | 5/1989 | Smith et al. |
| 4,844,610 A | 7/1989 | North, Jr. |
| 4,933,813 A | 6/1990 | Berger |
| 5,028,127 A | 7/1991 | Spitzberg |
| 5,030,002 A * | 7/1991 | North, Jr. .................. 356/73 |
| 5,040,890 A | 8/1991 | North, Jr. |
| 5,043,706 A | 8/1991 | Oliver |
| 5,083,862 A | 1/1992 | Rusnak |
| 5,138,868 A | 8/1992 | Long |
| 5,139,609 A | 8/1992 | Fields et al. |
| 5,150,037 A | 9/1992 | Kouzuki |
| 5,150,313 A | 9/1992 | van den Engh et al. |
| 5,155,543 A | 10/1992 | Hirako |
| 5,204,884 A | 4/1993 | Leary et al. |
| 5,224,058 A | 6/1993 | Mickaels et al. |
| 5,230,026 A | 7/1993 | Ohta et al. |
| 5,270,548 A | 12/1993 | Steinkamp |
| 5,301,685 A | 4/1994 | Guirguis |
| 5,308,990 A | 5/1994 | Takahashi et al. |
| 5,367,474 A | 11/1994 | Auer et al. |
| 5,374,395 A | 12/1994 | Robinson et al. |
| 5,395,588 A | 3/1995 | North, Jr. et al. |
| 5,403,552 A | 4/1995 | Pardikes |
| 5,466,946 A | 11/1995 | Kleinschmitt et al. |
| 5,469,375 A | 11/1995 | Kosaka |
| 5,539,386 A | 7/1996 | Elliott |
| 5,552,885 A | 9/1996 | Steen |
| 5,559,339 A | 9/1996 | Domanik et al. |
| 5,616,124 A | 4/1997 | Hague et al. |
| 5,684,480 A | 11/1997 | Jansson |
| 5,739,902 A | 4/1998 | Gjelsnes et al. |
| 5,797,430 A | 8/1998 | Becke et al. |
| 5,798,222 A | 8/1998 | Goix |
| 5,804,507 A | 9/1998 | Perlov et al. |
| 5,883,378 A | 3/1999 | Irish et al. |
| 5,920,388 A | 7/1999 | Sandberg et al. |
| 5,960,129 A | 9/1999 | Kleinschmitt |
| 5,981,180 A | 11/1999 | Chandler et al. |
| 6,016,376 A | 1/2000 | Ghaemi et al. |
| 6,039,078 A | 3/2000 | Tamari |
| 6,067,157 A | 5/2000 | Altendorf |
| 6,070,477 A | 6/2000 | Mark |
| 6,091,502 A | 7/2000 | Weigl et al. |
| 6,097,485 A | 8/2000 | Lievan |
| 6,108,463 A | 8/2000 | Herron et al. |
| 6,110,427 A | 8/2000 | Uffenheimer |
| 6,115,065 A | 9/2000 | Yadid-Pecht et al. |
| 6,139,800 A | 10/2000 | Chandler |
| 6,154,276 A | 11/2000 | Mariella, Jr. |
| 6,156,208 A | 12/2000 | Desjardins et al. |
| 6,181,319 B1 | 1/2001 | Fujita et al. |
| 6,183,697 B1 | 2/2001 | Tanaka et al. |
| 6,288,783 B1 | 9/2001 | Auad |
| 6,377,721 B1 | 4/2002 | Walt et al. |
| 6,382,228 B1 | 5/2002 | Cabuz et al. |
| 6,403,378 B1 | 6/2002 | Phi-Wilson et al. |
| 6,427,521 B2 | 8/2002 | Jakkula et al. |
| 6,431,950 B1 | 8/2002 | Mayes |
| 6,456,769 B1 | 9/2002 | Furusawa et al. |
| 6,469,787 B1 | 10/2002 | Meyer et al. |
| 6,473,171 B1 | 10/2002 | Buttry et al. |
| 6,519,355 B2 | 2/2003 | Nelson |
| 6,522,775 B2 | 2/2003 | Nelson |
| 6,568,271 B2 | 5/2003 | Shah et al. |
| 6,587,203 B2 | 7/2003 | Colon |
| 6,602,469 B1 | 8/2003 | Maus et al. |
| 6,636,623 B2 | 10/2003 | Nelson et al. |
| 6,675,835 B2 | 1/2004 | Gerner et al. |
| 6,694,799 B2 | 2/2004 | Small |
| 6,700,130 B2 | 3/2004 | Fritz |
| 6,710,871 B1 | 3/2004 | Goix |
| 6,718,415 B1 | 4/2004 | Chu |
| 6,778,910 B1 | 8/2004 | Vidal et al. |
| 6,809,804 B1 | 10/2004 | Yount et al. |
| 6,816,257 B2 | 11/2004 | Goix |
| 6,825,926 B2 | 11/2004 | Turner et al. |
| 6,852,284 B1 | 2/2005 | Holl et al. |
| 6,859,570 B2 | 2/2005 | Walt et al. |
| 6,869,569 B2 | 3/2005 | Kramer |
| 6,872,180 B2 | 3/2005 | Reinhardt et al. |
| 6,890,487 B1 * | 5/2005 | Sklar et al. .................. 422/93 |
| 6,897,954 B2 | 5/2005 | Bishop et al. |
| 6,901,964 B2 | 6/2005 | Kippe et al. |
| 6,908,226 B2 | 6/2005 | Siddiqui et al. |
| 6,912,904 B2 | 7/2005 | Storm, Jr. et al. |
| 6,936,828 B2 | 8/2005 | Saccomanno |
| 6,941,005 B2 | 9/2005 | Lary et al. |
| 6,944,322 B2 | 9/2005 | Johnson et al. |
| 7,009,189 B2 | 3/2006 | Saccomanno |
| 7,012,689 B2 | 3/2006 | Sharpe |
| 7,019,834 B2 | 3/2006 | Sebok et al. |
| 7,024,316 B1 | 4/2006 | Ellison et al. |
| 7,061,595 B2 | 6/2006 | Cabuz et al. |
| 7,075,647 B2 | 7/2006 | Christodoulou |
| 7,105,355 B2 | 9/2006 | Kurabayashi et al. |
| 7,106,442 B2 | 9/2006 | Silcott et al. |
| 7,113,266 B1 | 9/2006 | Wells |
| 7,130,046 B2 | 10/2006 | Fritz et al. |
| 7,232,687 B2 | 6/2007 | Lary et al. |
| 7,262,838 B2 | 8/2007 | Fritz |
| 7,274,316 B2 | 9/2007 | Moore |
| 7,328,722 B2 | 2/2008 | Rich |
| 7,362,432 B2 | 4/2008 | Roth |
| 7,403,125 B2 | 7/2008 | Rich |
| 7,471,393 B2 | 12/2008 | Trainer |
| 7,520,300 B2 | 4/2009 | Rich |
| 7,628,956 B2 | 12/2009 | Jindo |
| 7,738,099 B2 | 6/2010 | Morrell et al. |
| 7,739,060 B2 | 6/2010 | Goebel et al. |
| 7,776,268 B2 | 8/2010 | Rich |
| 7,780,916 B2 | 8/2010 | Bair et al. |
| 7,843,561 B2 | 11/2010 | Rich |
| 7,857,005 B2 | 12/2010 | Rich et al. |
| 7,903,706 B2 | 3/2011 | O'Shaughnessy et al. |
| 7,981,661 B2 | 7/2011 | Rich |
| 7,996,188 B2 | 8/2011 | Olson et al. |
| 8,017,402 B2 | 9/2011 | Rich |
| 8,031,340 B2 | 10/2011 | Rich et al. |
| 2001/0014477 A1 | 8/2001 | Pelc et al. |
| 2001/0039053 A1 | 11/2001 | Liseo et al. |
| 2002/0028434 A1 | 3/2002 | Goix et al. |
| 2002/0049782 A1 | 4/2002 | Herzenberg |
| 2002/0059959 A1 | 5/2002 | Qatu et al. |
| 2002/0080341 A1 | 6/2002 | Kosaka |
| 2002/0123154 A1 | 9/2002 | Burshteyn |
| 2002/0192113 A1 | 12/2002 | Uffenheimer et al. |
| 2003/0035168 A1 | 2/2003 | Qian et al. |
| 2003/0048539 A1 | 3/2003 | Oostman et al. |
| 2003/0054558 A1 | 3/2003 | Kurabayashi |
| 2003/0062314 A1 | 4/2003 | Davidson et al. |
| 2003/0072549 A1 | 4/2003 | Facer et al. |
| 2003/0078763 A1 | 4/2003 | Potts |
| 2003/0129090 A1 * | 7/2003 | Farrell .................. 422/68.1 |
| 2003/0134330 A1 | 7/2003 | Ravkin et al. |
| 2003/0148379 A1 | 8/2003 | Roitman et al. |
| 2003/0175157 A1 | 9/2003 | Micklash, II et al. |
| 2003/0202175 A1 | 10/2003 | Van den Engh et al. |
| 2003/0211009 A1 | 11/2003 | Buchanan |
| 2003/0223061 A1 | 12/2003 | Sebok |
| 2003/0235919 A1 | 12/2003 | Chandler |
| 2004/0031521 A1 | 2/2004 | Vrane et al. |
| 2004/0048362 A1 | 3/2004 | Trulson et al. |
| 2004/0112808 A1 | 6/2004 | Takagi et al. |
| 2004/0119974 A1 | 6/2004 | Bishop et al. |
| 2004/0123645 A1 | 7/2004 | Storm, Jr. et al. |
| 2004/0131322 A1 | 7/2004 | Ye et al. |
| 2004/0143423 A1 | 7/2004 | Parks et al. |
| 2004/0175837 A1 | 9/2004 | Bonne et al. |
| 2004/0197768 A1 | 10/2004 | Glencross |
| 2004/0201845 A1 | 10/2004 | Quist et al. |
| 2004/0246476 A1 | 12/2004 | Bevis et al. |
| 2005/0044110 A1 | 2/2005 | Herzenberg |
| 2005/0047292 A1 | 3/2005 | Park et al. |
| 2005/0057749 A1 | 3/2005 | Dietz et al. |

(56) References Cited

U.S. PATENT DOCUMENTS

| | | |
|---|---|---|
| 2005/0069454 A1 | 3/2005 | Bell |
| 2005/0073686 A1 | 4/2005 | Roth et al. |
| 2005/0078299 A1 | 4/2005 | Fritz et al. |
| 2005/0105091 A1 | 5/2005 | Lieberman et al. |
| 2005/0162648 A1 | 7/2005 | Auer et al. |
| 2005/0163663 A1 | 7/2005 | Martino et al. |
| 2005/0195605 A1 | 9/2005 | Saccomanno et al. |
| 2005/0195684 A1 | 9/2005 | Mayer |
| 2005/0252574 A1 | 11/2005 | Khan et al. |
| 2006/0002634 A1 | 1/2006 | Riley et al. |
| 2006/0015291 A1 | 1/2006 | Parks et al. |
| 2006/0023219 A1 | 2/2006 | Meyer et al. |
| 2006/0161057 A1 | 7/2006 | Weber |
| 2006/0177937 A1 | 8/2006 | Kurabayashi et al. |
| 2006/0219873 A1 | 10/2006 | Martin et al. |
| 2006/0280061 A1 | 12/2006 | Koreeda et al. |
| 2006/0281143 A1 | 12/2006 | Liu et al. |
| 2006/0286549 A1 | 12/2006 | Sohn et al. |
| 2007/0003434 A1 | 1/2007 | Padmanabhan et al. |
| 2007/0041013 A1 | 2/2007 | Fritz et al. |
| 2007/0079653 A1 | 4/2007 | Zuleta et al. |
| 2007/0096039 A1 | 5/2007 | Kapoor et al. |
| 2007/0124089 A1 | 5/2007 | Jochum et al. |
| 2007/0127863 A1 | 6/2007 | Bair et al. |
| 2007/0144277 A1 | 6/2007 | Padmanabhan et al. |
| 2007/0212262 A1 | 9/2007 | Rich |
| 2007/0224684 A1 | 9/2007 | Olson et al. |
| 2007/0243106 A1 | 10/2007 | Rich |
| 2008/0055595 A1 | 3/2008 | Olson et al. |
| 2008/0064113 A1 | 3/2008 | Goix et al. |
| 2008/0092961 A1 | 4/2008 | Bair et al. |
| 2008/0215297 A1 | 9/2008 | Goebel et al. |
| 2008/0228444 A1 | 9/2008 | Olson et al. |
| 2008/0246949 A1 | 10/2008 | Harris et al. |
| 2009/0104075 A1 | 4/2009 | Rich |
| 2009/0174881 A1 | 7/2009 | Rich |
| 2009/0201501 A1 | 8/2009 | Bair et al. |
| 2009/0202130 A1 | 8/2009 | George et al. |
| 2009/0216478 A1 | 8/2009 | Estevez-Labori |
| 2009/0257339 A1 | 10/2009 | Katayama |
| 2009/0260701 A1 | 10/2009 | Rich et al. |
| 2009/0293910 A1 | 12/2009 | Ball et al. |
| 2010/0008204 A1 | 1/2010 | Bae et al. |
| 2010/0012853 A1 | 1/2010 | Parks |
| 2010/0032584 A1 | 2/2010 | Dayong et al. |
| 2010/0118298 A1 | 5/2010 | Bair et al. |
| 2010/0119298 A1 | 5/2010 | Huang |
| 2010/0302536 A1 | 12/2010 | Ball et al. |
| 2010/0319469 A1 | 12/2010 | Rich |
| 2010/0319786 A1 | 12/2010 | Bair et al. |
| 2011/0008816 A1 | 1/2011 | Ball et al. |
| 2011/0058163 A1 | 3/2011 | Rich |
| 2011/0061471 A1 | 3/2011 | Rich et al. |
| 2011/0306031 A1 | 12/2011 | Rich |

FOREIGN PATENT DOCUMENTS

| | | | |
|---|---|---|---|
| EP | 1396736 A | 3/2004 | |
| EP | 1521076 | 4/2005 | |
| JP | Sho5913689 | 3/1984 | |
| JP | Sho6353901 | 4/1988 | |
| JP | 04086546 H | 3/1992 | |
| JP | 6194299 A | 7/1994 | |
| JP | 06221988 H | 12/1994 | |
| JP | 7260084 A | 10/1995 | |
| JP | 08201267 H | 8/1996 | |
| JP | 09288053 H | 11/1997 | |
| JP | 10227737 A | 8/1998 | |
| JP | 2001050887 A | 2/2001 | |
| JP | 2001170062 A | 6/2001 | |
| JP | 2003262201 A | 9/2003 | |
| JP | 200477484 | 3/2004 | |
| WO | 9956052 | 11/1999 | |
| WO | 0194914 | 12/2001 | |
| WO | 2005017499 | 2/2005 | |
| WO | WO/2005/017499 | 2/2005 | |
| WO | 2005068971 | 7/2005 | |
| WO | 2005073694 A | 8/2005 | |
| WO | 2005091893 | 10/2005 | |
| WO | 2006055722 A | 5/2006 | |
| WO | 2007/103969 | 3/2007 | |
| WO | 2007067577 A | 6/2007 | |
| WO | 2007100723 A | 9/2007 | |
| WO | WO 2007103969 A2 * | 9/2007 | ............ G01N 33/00 |
| WO | 2007136749 A | 11/2007 | |
| WO | 2008058217 A | 5/2008 | |
| WO | 2010/101623 | 9/2010 | |

\* cited by examiner

FLUIDIC SYSTEM FOR A FLOW CYTOMETER WITH TEMPORAL PROCESSING

CROSS-REFERENCE TO RELATED APPLICATIONS

This application claims the benefit of U.S. Provisional Application No. 60/829,300 filed 13 Oct. 2006 and entitled "Flow Cytometer System with Sampling Device", which is incorporated in its entirety by this reference.

This application is related to U.S. patent application Ser. No. 11/370,714 entitled "Fluidic System for a Flow Cytometer" and filed 8 Mar. 2006, which is incorporated in its entirety by this reference. This application is also related to U.S. patent application Ser. No. 11/297,667 entitled "Pulsation Attenuator For A Fluidic System" and filed 7 Dec. 2005, which is hereby incorporated in its entirety by this reference.

TECHNICAL FIELD

This invention relates generally to the flow cytometer field, and more specifically to an improved fluidic system in the flow cytometer field.

BACKGROUND

The fluidic system of a conventional flow cytometer incorporates an air and/or vacuum pump to pressurize and pump sheath fluid from a high-pressure container to the interrogation zone of a flow cell. These fluidic systems are typically arduous to assemble (which increases the costs of the flow cytometer), heavy to haul (which limits the repair options), and challenging to calibrate (which induces errors in the data). Thus, there is a need in the flow cytometer field to create an improved fluidic system. This invention provides such improved fluidic system for a flow cytometer.

DESCRIPTION OF THE PREFERRED EMBODIMENTS

The following description of the preferred embodiments of the invention is not intended to limit the invention to these preferred embodiments, but rather to enable any person skilled in the art to make and use this invention.

Figure 1:
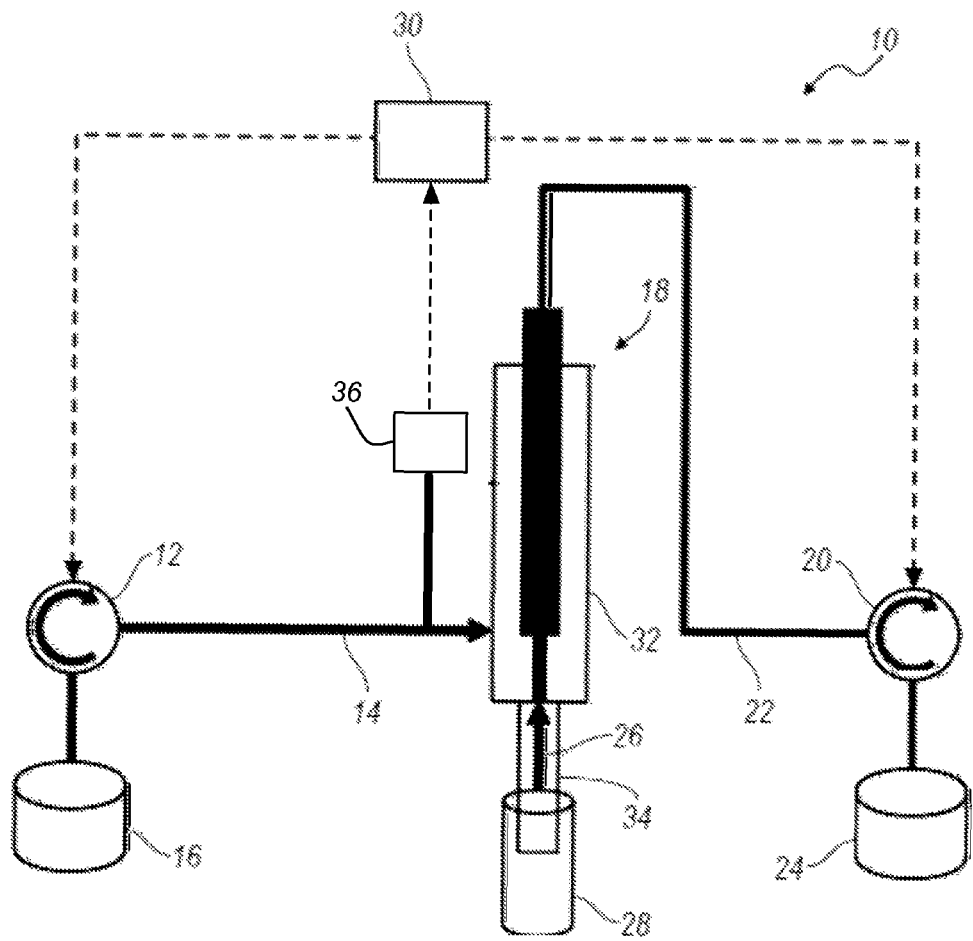
FIG. 1 is a schematic representation of the fluidic system of the preferred embodiment of the invention.

As shown in FIG. 1, the fluidic system 10 of the preferred embodiment includes a sheath pump 12 to pump sheath fluid 14 from a sheath container 16 through a sample port 34 into an interrogation zone 18 and a waste pump 20 to pump the sheath fluid 14 and a sample fluid 26 as waste fluid 22 from the interrogation zone 18 into a waste container 24, and a processor 30 to calculate a time window based on the flow rate of the sample fluid 26. Preferably the processor 30 also calculates a time window for the sample fluid to reach the interrogation zone 18 from the sample port 34 based on the flow rate of the sample fluid 26. The interrogation zone 18 functions to provide a location for the fluidic system 10 and an optical analysis system 32 of the flow cytometer to cooperatively facilitate the analysis of the sample fluid 26. The interrogation zone 18 is preferably surrounded by a conventional optical analysis system 32 (with light sources and light detectors), but any suitable analysis system may be used. The fluidic system 10 is preferably incorporated into a flow cytometer, but may be alternatively incorporated into any suitable system that pumps a first fluid from a first container into an interrogation zone, draws a second fluid from a second container into the interrogation zone, and pumps the combined fluids from the interrogation zone into a third container. The sample fluid 26 contains particles to be analyzed by the flow cytometer. The sample fluid 26 is preferably blood, but the sample fluid 26 may alternatively be any suitable fluid to be analyzed by the flow cytometer.

The sheath pump 12 of the preferred embodiment functions to pump sheath fluid 14 from a sheath container 16 into an interrogation zone 18. The sheath fluid 14 functions to hydrodynamically focus the sample fluid 26. The process of hydrodynamic focusing results in laminar flow of the sample fluid 26 and enables the optical system to illuminate, and thus analyze, the particles within the sample fluid 26 with uniformity and repeatability. Preferably, the sheath fluid 14 is buffered saline or de-ionized water, but the sheath fluid 14 may alternatively be any suitable fluid to hydrodynamically focus the sample fluid 26. The sheath container 16 functions to contain the sheath fluid 14. The sheath container 16 is preferably a vented tank with a volume of approximately 1 L, but the sheath tank may alternatively be any suitable container to contain the sheath fluid 14. Preferably, the sheath pump 12 is a positive displacement pump. More preferably, the sheath pump 12 is a peristaltic pump with a flexible tube and one or more cams that pump the sheath fluid 14 through the flexible tube. The sheath pump 12 preferably has a known flow rate to pump speed ratio, such that control of the speed of the sheath pump 12 corresponds to a control of the flow rate of the sheath fluid 14. With this pump type, the fluidic system 10 is relatively easy to assemble, light to haul, quick to control, and easy to clean. Alternatively, the sheath pump 12 may be any suitable pump that pumps sheath fluid 14 from a sheath container 16 into an interrogation zone 18.

The waste pump 20 of the preferred embodiment functions to pump the waste fluid 22 from the interrogation zone 18 into a waste container 24. Preferably, the waste fluid 22 includes the sheath fluid 14 and the sample fluid 26. Alternatively, the waste fluid 22 may include any fluid that exits the interrogation zone 18. The waste container 24 is preferably a vented tank with a volume of approximately 1 L, but the waste tank may alternatively be any suitable container to contain the waste fluid 22. Like the sheath pump 12, the waste pump 20 is preferably a positive displacement pump and more preferably a peristaltic pump with a flexible tube and one or more cams that pump the waste fluid 22 through the flexible tube. The waste pump 20 preferably has a known flow rate to pump speed ratio, such that control of the speed of the waste pump 20 corresponds to a control of the flow rate of the waste fluid 22. With this pump type, the fluidic system 10 is relatively easy to assemble, light to haul, quick to control, and easy to clean. Alternatively, the waste pump 20 may be any suitable pump that pumps waste fluid 22 from a waste container 24 into an interrogation zone 18.

The sheath pump 12 and the waste pump 20 preferably cooperate to draw the sample fluid 26 from the sample port 34 and through the interrogation zone 18 through the use of a pressure differential (e.g., the sheath pump 12 "pushes" the sheath fluid 14 and the waste pump 20 "pulls" the sheath fluid 14 and the sample fluid 26). In order to allow a variable flow rate of the sample fluid 26, the fluidic system 10 preferably allows for a variable flow rate of the sheath fluid 14 and/or the waste fluid 22. In a first variation, the sheath pump 12 and the waste pump 20 are driven by a single motor, but with a variable drive ratio device (e.g., transmission), such that the sheath pump 12 and the waste pump 20 may be operated at different pump speeds and, therefore, allow for a variable flow rate of the sheath fluid 14 and/or the waste fluid 22. In a second variation, the sheath pump 12 and the waste pump 20 are driven by a single motor, but the fluidic system 10 includes at least one by-pass valve located near the sheath pump 12 and/or the waste pump 20. The by-pass valve diverts a variable amount of the fluid flow and, therefore, allows for a variable flow rate of the sheath fluid 14 and/or waste fluid 22. In a third variation, the sheath pump 12 and the waste pump 20 are driven by a single motor, but the fluidic system 10 includes at least one restrictive valve located near the sheath pump 12 and/or the waste pump 20. The restrictive valve alters the fluid flow and, therefore, allows for a variable flow rate of the sheath fluid 14 and/or waste fluid 22. In a fourth variation, the sheath pump 12 and the waste pump 20 are driven by separate motors with separate controls and, therefore, allows for a variable flow rate of the sheath fluid 14 and/or waste fluid 22. The fluidic system 10 may, however, include other suitable variations that draw the sample fluid 26 from the sample port 34 and through the interrogation zone 18 through the use of a pressure differential.

The fluidic system 10 of the preferred embodiment also includes a pressure sensor 36 that functions to measure a pressure of the sheath fluid 14 as close as possible to the inlet for the sample fluid 26. This measured pressure is an adequate estimate for the pressure of the sample fluid 26. The pressure sensor 36 preferably measures a pressure differential between the top of the drawtube 34 near the flow cell 32 and the bottom of the drawtube 34 near the sample container 28, but may alternatively measure a pressure differential between the drawtube 34 and atmosphere. The controller 30 is preferably connected to the pressure sensor 36 and adjusts the flow rate of the sample fluid 26 based on the measured pressure. The controller 30 may alternatively or additionally be connected to other suitable devices to assist in the control of the flow rate of the sample fluid 26. In a first variation, the fluidic system 10 may include a flow meter that functions to measure the flow rate of the sample fluid 26 from the sample container 28 into the interrogation zone 18. In a second variation, the fluidic system 10 may include an input device that functions to receive information related to a fluidic resistance of a drawtube 34 that transports the sample fluid 26 from the sample container 28 into the interrogation zone 18. The input device is preferably an optical device (e.g., a bar code scanner) or an electromagnetic device (e.g., a RFID receiver) that functions to automatically scan and read a code on the drawtube 34. The code is preferably cross-referenced with empirically derived information regarding the fluidic resistance of the drawtube 34. The input device may alternatively be a user-interface device that accepts a code or value related to the fluidic resistance of the drawtube 34. In a third variation, the fluidic system 10 may be substantially self-calibrating according to the following steps: the user places a drawtube 34 of the flow cell 32 into a known fluid (such as buffered saline), the user pumps waste fluid 22 from the interrogation zone 18 into a waste container 24 while maintaining a negligible flow rate of the sheath fluid 14 thereby drawing the known fluid through the drawtube 34 and into the interrogation zone 18, and the fluidic system 10 (through measurement of the flow rate of the waste fluid 22 or any other suitable parameter) estimates the resistance of the drawtube 34. With this estimated resistance of the drawtube 34 for the flow cell 32 combined with the measured pressure of the sheath fluid 14, the controller 30 adjusts the flow rate of the sample fluid 26 with greater accuracy and control.

The processor 30 of the preferred embodiment functions to adjust the flow rate of the sample fluid 26 from the sample port 34 and through the interrogation zone 18. Preferably, the processor 30 adjusts the flow rate of the sample fluid 26 by adjusting the variable flow rate of the sheath fluid 14 and/or the waste fluid 22. More preferably, the processor 30 adjusts the flow rate of the sample fluid 26 by allowing an adjustable flow rate of the sheath fluid 14 from the sheath container 16 to the interrogation zone 18, while maintaining a consistent flow rate of the waste fluid 22 from the interrogation zone 18 into the waste container 24. The advantage of this arrangement is a finer control of the flow rate of the sample fluid 26. Alternatively, the processor 30 may adjust the flow rate of waste fluid 22 while maintaining the flow rate of the sheath fluid 14, or may simultaneously adjust the flow rates of the sheath fluid 14 and the waste fluid 22. Furthermore, the processor 30 may employ one technique (such as allowing an adjustable flow rate of the sheath fluid 14, while maintaining a consistent flow rate of the waste fluid 22) in most situations, and may employ another technique (such as simultaneously adjusting the flow rates of the sheath fluid 14 and the waste fluid 22) in other situations to quickly response to a user input. The processor is preferably an embedded microprocessor, but may be a computer system, or any other suitable type of processor.

The processor 30 also preferably includes a device or method to determine or estimate the flow rate of the sample. Combining a known flow rate of the sample with a known (preferably either predetermined or measured) volume between the sample port 34 and the interrogation zone 18, the processor 30 can calculate a time window for a sample to reach the detection zone. The processor 30 also preferably functions to control the optical analysis system 32 of the flow cytometer system. Preferably based on the processor calculated timing for the sample to reach the interrogation zone 18, the processor 30 preferably instructs the optical analysis system 32 to stop data collection shortly before the end of one sample and begin collection of data for the next sample shortly after the entry of the next sample into the detection zone. This process preferably continues for the other samples. Due to the intrinsic nature of capillary flow, the flow cytometer system minimizes, if not completely eliminates, mixing between successive unseparated sample zones. Any mixing of the samples that does occur can be excluded from data collection by an adjustment of the timing of the data collection or by an electronic adjustment of the collected data. The processor 30 preferably performs such an adjustment of either the optical analysis system or by filtering the collected data. The use of peristaltic pumps with accurate flow rate control aids in the timing and precision of the data collection.

The fluidic system 10 of the preferred embodiment also includes a multi-sampling device 28. The multi-sample sampling device 28 functions to analyze successive samples through a capillary sample device without a physical separation between the samples. The multi-sampling device 28 (which can be either automated or manual) preferably draws from samples in multiple wells, tubes, containers, or any other suitable device. The multi-sampling device 28 is preferably a conventional automated sample handling device, such as a GILSON 215 liquid manager, or any suitable device that analyzes successive samples through a capillary sample device without a physical separation between the samples. The multi-sampling device 28 may alternatively be a carousel sample handler, a TECAN brand sampling system for microplates, a microplate on a moveable stage, a plurality of valves and/or syringes, or any of the multiple sample handling methods and apparatuses that are described in U.S. Pat. No. 6,878, 556, which is incorporated in its entirety by this reference. The multi-sampling device 28 is preferably connected to a sample port 34, which functions as an interface for the sample fluid 26 between the multi-sample sampling device 28 and the interrogation zone 18.

Figure 2:
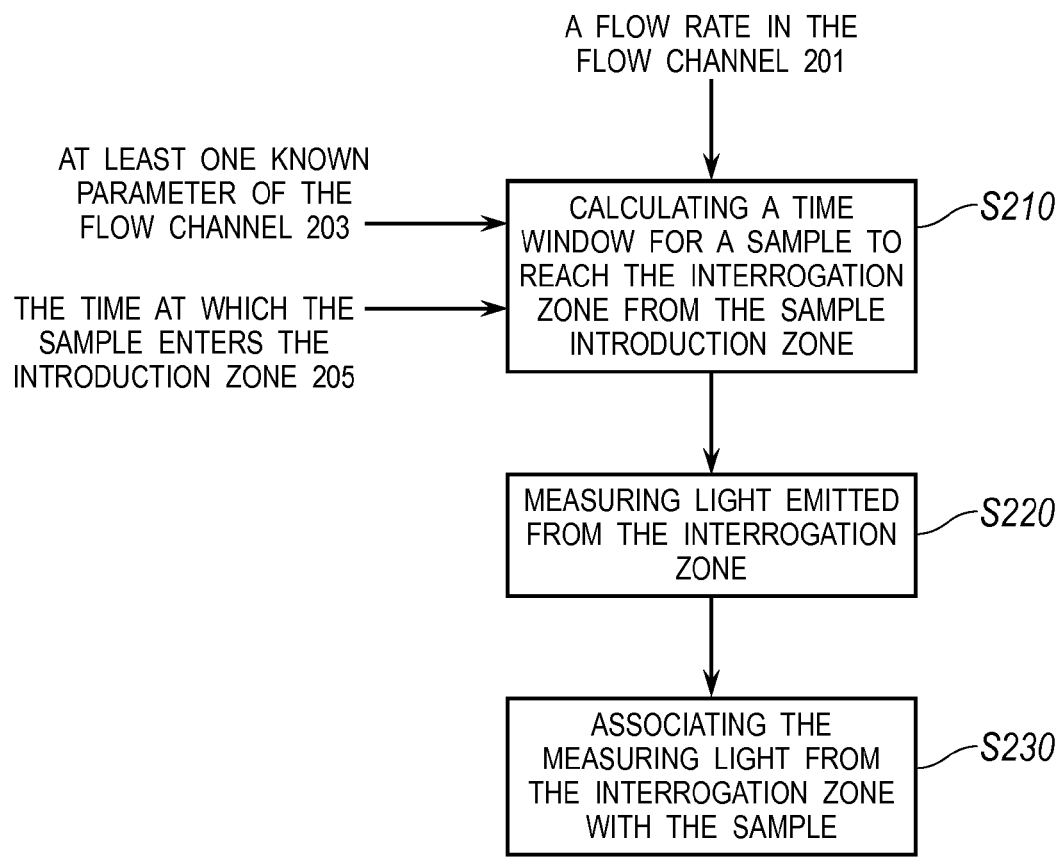
FIG. 2 is a flowchart representation of a first preferred embodiment of the invention.

As shown in FIG. 2, a method of measuring successive samples as the samples pass through a sample port into the interrogation zone of a flow channel in a flow cytometer system includes the steps of calculating a time window for a sample to reach the interrogation zone from the sample port S210 based on at least one flow rate in the flow channel 201, and at least one known parameter of the flow channel 203, measuring light emitted from the interrogation zone S220, and associating the measured light from the interrogation zone, with the sample S230.

Step S210, which recites calculating a time window for a sample to reach the interrogation zone from the sample port, functions to calculate the time for a sample to travel from the sample port to the interrogation zone of a flow cytometer system, based on at least one flow rate in the flow channel 201, and at least one known parameter of the flow channel 203. The known parameters 203 may include the length of the flow channel, the volume of the flow channel, material properties, such as fluid friction, of the material of which the flow channel is fabricated, or any other suitable parameter that may be used to calculate the flow rate. More preferably the time at which the sample enters the sample port 205 is also input to step S210. In one variation of step S210, a buffer fluid (either a gas or a liquid) may be inserted between samples.

Step S220, which recites measuring light emitted from the interrogation zone, functions to measure the light emitted by the sample as it is excited by the optical system of a flow cytometer, as it passes through the interrogation zone of a flow cytometer. Preferably, the emitted light is measured after the calculation of the time window corresponding to each sample and, more preferably, the timing of the measurement of the emitted light may be adjusted to correspond to the beginning and end of each sample. In a first variation, the measured light may be used to detect interfering samples. In a second variation, the timing of the emitted light measurement may be adjusted to measure only the non-interfering portions of successive samples. In yet another variation, in a third variation the light measured may be controlled such that no contaminated or mixed sample data is collected. In a fourth variation the light may be filtered to extract, remove, or reduce interfered samples.

S230, which recites associating the measured light from the interrogation zone with the sample, functions to associate the measured light with the sample that emitted the light. Preferably, the calculated time window from S210 is used as a time delay to associate the sample with the measured light. Preferably, if a sample is contaminated or mixed with another sample, then the sample data is discarded from the measurement.

As a person skilled in the art will recognize from the previous detailed description and from the figures and claims, modifications and changes can be made to the preferred embodiments of the invention without departing from the scope of this invention defined in the following claims.

We claim:

1. A fluidic system for pumping sample fluid from a sample port and into an interrogation zone of a flow cytometer, comprising:
   a sheath pump that pumps sheath fluid from a sheath container into an interrogation zone, wherein the sheath pump is configured fluidically between the sheath container and the interrogation zone;
   a waste pump that pumps waste fluid from the interrogation zone into a waste container, wherein the waste pump is configured fluidically between the interrogation zone and the waste container;
   wherein the sheath pump and the waste pump are configured to cooperatively draw a plurality of samples of sample fluid, through use of a pressure differential, from the sample port into the interrogation zone of the flow cytometer,
   an optical analysis system that stimulates emission of light from each of the plurality of samples in the interrogation zone and detects emitted light from each of the plurality of samples, wherein the optical analysis system collects data based on the emitted light; and
   a processor that adjusts a flow rate of the sample fluid from the sample port into the interrogation zone and that calculates a time window for each sample to reach the interrogation zone from the sample port based on the flow rate of the sample fluid, wherein the processor delays data collection by the time window to associate the emitted light with at least one of the plurality of samples.

2. The fluidic system of claim 1, wherein the processor and at least one of the sheath pump and waste pump are configured to adjust at least one of a flow rate of the sheath fluid and a flow rate of the waste fluid to adjust the flow rate of the sample fluid from the sample port into the interrogation zone of the flow cytometer.

3. The fluidic system of claim 2, wherein the processor adjusts the flow rate of the sample fluid by allowing an adjustable flow rate of the sheath fluid from the sheath container to the interrogation zone, while maintaining a consistent flow rate of the waste fluid from the interrogation zone into the waste container.

4. The fluidic system of claim 1, further comprising a multisampling device coupled to the sample port and adapted to introduce the plurality of samples through the sample port.

5. The fluidic system of claim 4, wherein the multisampling device inserts a buffer fluid between successive samples of the plurality of samples.

6. The fluidic system of claim 4, wherein a region between the sample port and the interrogation zone defines a known fixed volume and wherein the time window is based on the flow rate of the sample fluid and the known fixed volume.

7. The fluidic system of claim 4, wherein the processor identifies interfering samples.

8. The fluidic system of claim 1, wherein the processor identifies interfering samples.

9. The fluidic system of claim 8, wherein the processor is configured to adjust a timing of data collection after identifying interfering samples.

10. The fluidic system of claim 9, wherein the processor is configured to adjust the timing of the data collection to collect data from only non-interfering samples.

11. The fluidic system of claim 8, wherein the processor is configured to filter collected data after identifying interfering samples.

12. The fluidic system of claim 11, wherein the processor discards data from interfering samples.

13. The fluidic system of claim 1, wherein the processor instructs the optical analysis system to stop data collection before an exit of one sample from the interrogation zone and to begin data collection after an entry of a subsequent sample into the interrogation zone.

14. The fluidic system of claim 1, wherein at least one of the sheath and waste pumps is a peristaltic pump.

15. The fluidic system of claim 1, further comprising a drawtube that is coupled to the sample container and conveys the sample fluid from the sample container to the interrogation zone and a pressure sensor that measures a pressure differential of the sample fluid between the top of the drawtube and the bottom of the drawtube.

16. A fluidic system for pumping sample fluid from a sample port and into an interrogation zone of a flow cytometer, comprising:
- a sheath pump that pumps sheath fluid from a sheath container into an interrogation zone, wherein the sheath pump is configured fluidically between the sheath container and the interrogation zone;
- a waste pump that pumps waste fluid from the interrogation zone into a waste container, wherein the waste pump is configured fluidically between the interrogation zone and the waste container;
- wherein the sheath pump and the waste pump are configured to cooperatively draw a plurality of samples of sample fluid, through use of a pressure differential, from the sample port into the interrogation zone of the flow cytometer;
- an optical analysis system that stimulates emission of light from each of the plurality of samples in the interrogation zone and collects data based on detection of emitted light from each of the plurality of samples;
- a processor that adjusts a flow rate of the sample fluid from the sample port into the interrogation zone and that instructs the optical analysis system to stop data collection before an exit of one sample from the interrogation zone and to begin data collection after an entry of a subsequent sample into the interrogation zone, to associate the emitted light with at least one of the plurality of samples.

17. The fluidic system of claim 16, wherein the processor identifies interfering samples.

18. The fluidic system of claim 17, wherein the processor is configured to adjust a timing of data collection after identifying interfering samples.

19. The fluidic system of claim 18, wherein the processor is configured to adjust the timing of data collection to collect data from only non-interfering samples.

20. The fluidic system of claim 17, wherein the processor is configured to filter the collected data after identifying interfering samples.

21. The fluidic system of claim 20, wherein the processor discards data from interfering samples.

* * * * *